(12) United States Patent
Hulskotter et al.

(10) Patent No.: US 11,421,188 B2
(45) Date of Patent: Aug. 23, 2022

(54) LIQUID COMPOSITIONS THAT INCLUDE DELIVERY PARTICLES

(71) Applicant: The Procter & Gamble Company, Cincinnati, OH (US)

(72) Inventors: Frank Hulskotter, Bad Duerkheim (DE); Johan Smets, Lubbeek (BE); Cédric Marc Tahon, Oost-Vlaanderen (BE); Susana Fernandez Prieto, Benicarlo Castellon (ES); Jean-Francois Bodet, Waterloo (BE); Marianna Mamusa, Prato (IT); Piero Baglioni, Fiesole Firenza (IT)

(73) Assignee: The Procter & Gamble Company, Cincinnati, OH (US)

( * ) Notice: Subject to any disclaimer, the term of this patent is extended or adjusted under 35 U.S.C. 154(b) by 144 days.

(21) Appl. No.: 16/877,524

(22) Filed: May 19, 2020

(65) Prior Publication Data
US 2020/0369986 A1 Nov. 26, 2020

(30) Foreign Application Priority Data
May 22, 2019 (EP) .................................... 19175821

(51) Int. Cl.
C11D 3/37 (2006.01)
C11D 3/386 (2006.01)
C11D 3/50 (2006.01)

(52) U.S. Cl.
CPC ............ *C11D 3/3788* (2013.01); *C11D 3/386* (2013.01); *C11D 3/505* (2013.01)

(58) Field of Classification Search
CPC ... C11D 3/505; C11D 11/0017; C11D 3/3788; C11D 11/0094; C11D 17/0008; C11D 17/0013; C11D 1/72; C11D 3/0015; C11D 3/32; C11D 3/3776
See application file for complete search history.

(56) References Cited

U.S. PATENT DOCUMENTS

| | | | |
|---|---|---|---|
| 6,946,004 B2 * | 9/2005 | Huff | C08F 283/06 8/115.58 |
| 8,158,686 B2 | 4/2012 | Bouillo | |
| 10,538,631 B2 | 1/2020 | Aouad | |
| 10,556,995 B2 | 2/2020 | Aouad | |
| 2004/0266655 A1 | 12/2004 | Baum | |
| 2008/0255326 A1 | 10/2008 | Widmaier | |
| 2010/0204425 A1 | 8/2010 | Mertoglu | |
| 2013/0150277 A1 | 6/2013 | Fischer | |
| 2016/0362644 A1 | 12/2016 | Meine | |
| 2018/0028472 A1 | 2/2018 | Bamscheid | |
| 2018/0305636 A1 | 10/2018 | Kolter | |
| 2019/0076361 A1 | 3/2019 | Onoue | |
| 2020/0115506 A1 | 4/2020 | Aouad | |

FOREIGN PATENT DOCUMENTS

| | | |
|---|---|---|
| EP | 3126478 B1 | 9/2018 |
| WO | WO2006130442 A1 | 12/2006 |

OTHER PUBLICATIONS

Ananya Rajkumari, et al.; Preparation and Characterization of PLGA Nanoparticles Using Soluplus® as a Surfactant; World Journal of Pharmacy and Pharmaceutical Sciences vol. 6, Issue 12, 2017; pp. 629-641; Research Article; ISSN 2278-4357; www.wjpps.com.
Arianna Bartolini, et al.; Poly(ethylene glycol)-graft-poly(vinyl acetate) single-chain nanoparticles for the encapsulation of small molecules; Phys.Chem.Chem.Phys.; 2017; 19; pp. 4553-4559.
Extended European Search Report; Application No. 19175821.8-1114; dated Nov. 11, 2019; 8 pages.
Soluplus Brochure; BASF The Chemical Company; Pharma Ingredients & Services; Jul. 2010; Supersedes issue dated May 2010; 8 pages.
International Search Report and Written Opinion; Application Ser. No. PCT/US2020/070062 dated Aug. 26. 2020, 12 pages.

* cited by examiner

Primary Examiner — John R Hardee
(74) Attorney, Agent, or Firm — Gregory S. Darley-Emerson

(57) ABSTRACT

Liquid consumer product compositions that include delivery particles and a consumer product adjunct, where the delivery particles include a graft copolymer and a benefit agent, and where the graft copolymer includes a polyalkylene glycol, vinyl acetate moieties, and N-vinylcaprolactam moieties. Methods of making and using such particles and compositions.

17 Claims, No Drawings

LIQUID COMPOSITIONS THAT INCLUDE DELIVERY PARTICLES

FIELD OF THE INVENTION

The present disclosure relates to liquid consumer product compositions that include delivery particles and a consumer product adjunct, where the delivery particles includes a graft copolymer and a benefit agent, the graft copolymer including a polyalkylene glycol, vinyl acetate moieties, and N-vinylcaprolactam moieties. The present disclosure also relates to methods of making and using such particles and compositions.

BACKGROUND OF THE INVENTION

Manufacturers of consumer product compositions are continually seeking ways to improve the delivery and/or stability of benefit agents. Delivery particles that include the benefit agent can be useful in such compositions.

However, traditional encapsulation techniques, such as those that leading core-shell particles, are can be costly. Furthermore, the encapsulating material may not provide a direct benefit during intended application.

Certain graft copolymers have been disclosed as being useful for making delivery particles, but it is desirable to find improved and/or alternative particles. It may also be useful to find novel applications for commercially available polymers.

Furthermore, it can be challenging to formulate hydrophobic ingredients, such as hydrophobic perfume raw materials, in highly aqueous products.

There is a need for improved consumer product compositions that include delivery particles, as well as needs for making and using such compositions.

SUMMARY OF THE INVENTION

The present disclosure relates to delivery particles, liquid consumer product compositions that include delivery particles, and related methods and feedstock compositions.

For example, the present disclosure relates to a liquid consumer product composition that includes delivery particles and a consumer product adjunct, the delivery particles including a graft copolymer and a benefit agent, where the graft copolymer includes a polyalkylene glycol as a graft base and one or more side chains, and where the side chains including vinyl acetate moieties and N-vinylcaprolactam moieties.

The present disclosure also relates to a method of making a liquid consumer product composition, where the method includes the steps of: providing a liquid feedstock composition that includes a benefit agent and a graft copolymer, the graft copolymer including a polyalkylene glycol as a graft base and one or more side chains that include vinyl acetate moieties and N-vinylcaprolactam moieties; combining the feedstock composition with a base composition, where the base composition includes a consumer product adjunct, where the resulting liquid consumer product composition includes delivery particles that include the benefit agent and the graft copolymer.

The present disclosure also relates to a liquid consumer product composition obtainable by the methods described herein.

The present disclosure also relates to a process of treating a surface, the process including the step of contacting the surface with a liquid consumer product composition according to the present disclosure.

DETAILED DESCRIPTION OF THE INVENTION

The present disclosure relates to delivery particles, consumer product compositions that include such particles, and related processes. The particles typically include a graft copolymer and a benefit agent, where the graft copolymer is obtainable from a polyalkylene glycol (such as polyethylene glycol), vinyl acetate moieties, and N-vinylcaprolactam moieties. For example, when the graft copolymer and the benefit agent are premixed as a feedstock composition and then added to a base composition, the graft copolymer and benefit agent may self-assemble into particles, thereby saving processing time and cost that may be associated with traditional particles.

Without wishing to be bound by theory, it is believed that the presence of the vinylcaprolactam moieties in the graft copolymer contributes to hydrophobic domains in the resulting particles, even more than the vinyl acetate moieties of other, known graft copolymers. The resulting particles can result in improved benefit agent delivery and/or stability, particularly in the case of hydrophobic benefit agents, such as perfume oils, in aqueous product matrices, such as those common in liquid fabric conditioning products. Furthermore, it is believed that such particles can "protect" or otherwise partition the benefit agent from the rest of the liquid product matrix. This may inhibit undesirable reactions with other components of the product, such as those between perfumes and amines that may otherwise result in undesirable color changes, or between certain enzymes and water that may otherwise result in loss of enzyme activity. Without being further bound by theory, it is believed that the cationic conditioning agents of such liquid fabric conditioning products can further interact with the hydrophobic portions of such graft copolymers, thereby facilitating improved delivery of the conditioning agent, resulting in improved softening/conditioning benefits.

The particles, compositions, and related processes of the present disclosure are discussed in more detail below.

As used herein, the articles "a" and "an" when used in a claim, are understood to mean one or more of what is claimed or described. As used herein, the terms "include," "includes," and "including" are meant to be non-limiting. The compositions of the present disclosure can comprise, consist essentially of, or consist of, the components of the present disclosure.

The terms "substantially free of" or "substantially free from" may be used herein. This means that the indicated material is at the very minimum not deliberately added to the composition to form part of it, or, preferably, is not present at analytically detectable levels. It is meant to include compositions whereby the indicated material is present only as an impurity in one of the other materials deliberately included. The indicated material may be present, if at all, at a level of less than 1%, or less than 0.1%, or less than 0.01%, or even 0%, by weight of the composition.

As used herein the phrase "fabric care composition" includes compositions and formulations designed for treating fabric. Such compositions include but are not limited to, laundry cleaning compositions and detergents, fabric softening compositions, fabric enhancing compositions, fabric freshening compositions, laundry prewash, laundry pretreat, laundry additives, spray products, dry cleaning agent or composition, laundry rinse additive, wash additive, post-rinse fabric treatment, ironing aid, unit dose formulation, delayed delivery formulation, detergent contained on or in a porous substrate or nonwoven sheet, and other suitable forms that may be apparent to one skilled in the art in view of the teachings herein. Such compositions may be used as a pre-laundering treatment, a post-laundering treatment, or may be added during the rinse or wash cycle of the laundering operation.

Unless otherwise noted, all component or composition levels are in reference to the active portion of that component or composition, and are exclusive of impurities, for example, residual solvents or by-products, which may be present in commercially available sources of such components or compositions.

All temperatures herein are in degrees Celsius (° C.) unless otherwise indicated. Unless otherwise specified, all measurements herein are conducted at 20° C. and under the atmospheric pressure.

In all embodiments of the present disclosure, all percentages are by weight of the total composition, unless specifically stated otherwise. All ratios are weight ratios, unless specifically stated otherwise.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Liquid Consumer Product Composition

The present disclosure relates to liquid consumer product composition. The compositions may be liquid detergent compositions, for example compact liquid detergent compositions. The compositions may be fabric care compositions, hard surface cleaner compositions, dish care compositions, hair care compositions, body cleansing compositions, or mixtures thereof.

The compositions of the present disclosure may be fabric care compositions. Such compositions may be used as a pre-laundering treatment, a post-laundering treatment, or may be added during the rinse or wash cycle of the laundering operation.

The composition may be selected from the group of heavy duty liquid detergent compositions, light duty liquid detergents compositions, detergent gels commonly used for laundry, bleaching compositions, laundry additives, fabric enhancer compositions, and mixtures thereof. The composition may be a compact heavy duty liquid detergent composition. Other non-limiting examples of liquid compositions according to the present disclosure include shampoos, body cleansing compositions, and the like.

The composition may be in the form of a unitized dose article, such as a pouch. Such pouches typically include a water-soluble film, such as a polyvinyl alcohol water-soluble film, that at least partially encapsulates a composition. Suitable films are available from MonoSol, LLC (Indiana, USA). The composition can be encapsulated in a single or multi-compartment pouch. A multi-compartment pouch may have at least two, at least three, or at least four compartments. A multi-compartmented pouch may include compartments that are side-by-side and/or superposed. The composition contained in the pouch or compartments thereof may be liquid, solid (such as powders), or combinations thereof; in such cases, at least one encapsulated composition is a liquid composition. Unit dose articles such as pouches, as well as water-soluble films, are described in more detail below.

The composition may be characterized by a viscosity. The composition may have a viscosity of from about 1 to about 1500 centipoises (about 1-1500 mPa*s), from about 100 to 1000 centipoises (about 100-1000 mPa*s), or from about 200 to 500 centipoises (about 200-500 mPa*s) at 20 $s^{-1}$ and 21° C., is disclosed. Viscosity is determined according to the method provided in the Test Methods section below.

Delivery Particles (or "Particles")

The present disclosure relates to delivery particles, also simply called "particles" in the present disclosure. The particles comprise a graft copolymer and one or more benefit agents.

The one or more benefit agents may be encapsulated in at least one graft copolymer, and/or embedded in at least one graft copolymer. Compositions of the present disclosure may comprise the presently described particles.

The particles of the present disclosure may be present in a population, which may have a number-weighted average diameter (or "diameter" as used herein). Number-weighted average diameter is determined according to the method provided in the test method section below. The particles may have a number-weighted average diameter of (a) from about 0.5 microns to about 5000 microns, preferably from about 0.5 microns to about 1000 microns, more preferably from about 0.5 microns to about 250 microns, most preferably from about 1 microns to about 60 microns, and/or (b) from about 0.01 microns to about 0.5 microns, preferably from about 0.02 microns to about 0.5 microns, more preferably from about 0.04 microns to about 0.5 microns, and/or (c) from about 250 microns to about 10,000 microns, preferably from about 250 microns to about 7500 microns, more preferably from about 500 microns to about 5000 microns, most preferably from about 750 microns to about 2500 microns. The compositions of the present disclosure may have mixtures of particles having number-weighted average diameters according to (a), (b), and/or (c).

The particles of the present disclosure may be characterized by a self-assembly index of from about 1 to about 100. The particles of the present disclosure may be characterized by a SAXS index of from about 1 to about 100. The particles of the present disclosure may be characterized by a Dissolution Index, for example a Dissolution Index of 1. Test methods to determine the self-assembly index, the SAXS index, and/or the Dissolution Index may be found in US2018/0071201 to The Procter & Gamble Company, paragraphs [0177]-[0274], incorporated herein by reference.

One or more particles of the present disclosure may comprise at least one region comprising a benefit agent, such as a perfume raw material or enzyme. The region may comprise a benefit agent, such as a perfume raw material or enzyme, being encompassed or encapsulated within the graft copolymer. The region may comprise a benefit agent, such as a perfume raw material or enzyme, being embedded, for example partially embedded, within the graft copolymer.

One or more particles of the present disclosure may have a structure selected from the group consisting of: (a) a particle comprising a single region having benefit agent that is embedded in said at least one graft copolymer; (b) a particle comprising at least two regions having benefit agents that are embedded in said at least one graft copolymer; (c) a particle comprising at least one region having benefit agents that is at least partially embedded on the surface of at least one graft copolymer; (d) a particle comprising a single region having a benefit agent that is embedded in the graft copolymer and at least one region having a benefit agent that is at least partially embedded on the surface of the at least one graft copolymer; and (e) a particle comprising at least two regions having benefit agents that are embedded in the at least one graft copolymer and at least one region having a benefit agent that is at least partially embedded on the surface of the at least one polymer. Compositions of the present disclosure may include one or more particles having a structure according to (a)-(e), or mixtures thereof.

The particles may be characterized by a weight ratio of the benefit agent (e.g., perfume raw material and/or enzyme) to the graft copolymer. The weight ratio of the benefit agent to the graft copolymer may be from about 1:20 to about 20:1, preferably from about 4:1 to 20:1 are disclosed. The weight ratio is the ratio between the total weight of the benefit agent and the total weight of the graft copolymers in the population of particles. For the purposes of this ratio, the total weight of the benefit agent and/or the graft copolymers does not include free benefit agent and/or free graft copolymers in the composition that are not part of a particle.

The graft copolymers and the benefit agents of the particles are described in more detail below.

a. Graft Copolymer

The delivery particles of the present disclosure comprise a graft copolymer. The graft copolymers may comprise a polyalkylene glycol as a graft base and one or more side chains. The side chains may comprise vinyl acetate moieties and N-vinylcaprolactam moieties. By "vinyl acetate moieties," it is meant moieties derived from vinyl acetate monomers. By "N-vinylcaprolactam moieties," it is meant moieties derived from vinylcaprolactam monomers.

A graft copolymer molecule includes of a polymeric main chain, typically constituted of a long sequence of one monomer (the backbone), on which one or more polymeric side chains, constituted of one or more types of monomers of a different chemical nature than the backbone, are attached. In graft copolymers, a large number of parameters can be varied: the chemical nature, the molecular weight and the molecular weight distribution (MWD) of both the backbone and of the grafts, and the graft density along the backbone. Therefore, graft copolymers represent materials combining the properties of two or more polymers in one entity. Provided appropriate polymerization methods are used, tailor-made graft copolymers can be obtained. In common graft copolymers, the branches are randomly distributed along the backbone. The backbone and the branches may be homo- or copolymers but they differ in chemical nature or composition. Under the synthetic conditions used herein, the graft copolymer may also contain low levels of backbone homopolymer and side-chain graft homopolymer in addition to the graft copolymer itself.

By varying the nature and ratios of the polymers used in the backbone and in the graft, it is possible to obtain graft co-polymers of different amphiphilicity. Suitable graft copolymers according to the present disclosure may include graft copolymers comprising a few long chains comprising polyvinylacetate (PVAc) moieties and vinylcaprolactam moieties, hanging off a Polyethylene (PEG) backbone. The graft co-polymer normally has only few graft points (only 1-3 side chain grafts per the whole PEG chain, where the PEG chain is about 140 units long) with long side chains that include PVAc and vinylcaprolactam moieties The graft copolymer of the present disclosure may include a polyalkylene backbone, preferably a polyalkylene glycol backbone. Preferably, the polyalkylene glycol comprises a material selected from the group consisting of polyethylene glycol, polypropylene glycol, polybutylene glycol and mixtures thereof, more preferably said polyalkylene glycol comprises polyethylene glycol, are disclosed. Most preferably, the graft copolymer comprises a polyethylene glycol ("PEG") backbone.

The graft copolymer may comprise polyalkylene glycol, vinyl acetate, and vinylcaprolactam. The graft copolymer may comprise a polyalkylene glycol backbone comprising vinyl acetate moieties and vinyl caprolactam moeities that are covalently attached to said polyalkylene glycol backbone, preferably said co-polymer of polyalkylene glycol comprises polyethylene glycol.

The graft copolymer may comprise at least one copolymer of polyalkylene glycol, vinyl acetate, and vinylcaprolactam that has from 1 to about 10 side chain grafts per polyalkylene glycol backbone, preferably said copolymer has from 1 to about 5 side chain grafts per polyalkylene glycol backbone, more preferably from about 1 to about 3 side chain grafts per polyalkylene glycol backbone, most preferably about 1 side cahin graft per polyalkylene glycol backbone, where preferably the copolymer of polyalkylene glycol comprises polyethylene glycol.

The copolymer may have, on average, based on the reaction mixture obtained, not more than 1 graft site, preferably not more than 0.6 graft site, more preferably not more than 0.5 graft site and most preferably not more than 0.4 graft site per 50 alkylene oxide units. They may comprise, on average, based on the reaction mixture obtained, preferably at least 0.05, in particular at least 0.1 graft site per 50 alkylene oxide units. The degree of branching can be determined, for example, by means of $^{13}C$ NMR spectroscopy from the integrals of the signals of the graft sites and the —CH2-groups of the polyalkylene oxide.

The graft copolymer may include vinyl acetate monomers that have hydrolyzed, effectively resulting in hydroxyl-containing polyvinyl alcohol monomers in the graft copolymer. Thus, the graft copolymer may be characterized by a degree of hydrolysis. Typically, the degree of hydrolysis is relatively low, such as less than 30 mol %, or less than 20 mol %, or less than 10 mol %, or less than 5 mol %, or less than 3 mol %, or from about 0.1 mol % to about 3 mol %. The degree of hydrolysis, as mol %, is based on the total moles of polyvinyl acetate originally present in the graft copolymer, or, after hydrolysis has occurred, the combined moles of polyvinyl alcohol monomers and polyvinyl acetate monomers in the graft copolymer. A relatively low degree of hydrolysis may be preferred so that the copolymer maintains sufficient amphiphilic character; it is believed that as more polyvinyl acetate moieties are hydrolyzed, relatively hydrophobic character is lost, and particles are formed less effectively, particularly in aqueous environments. The degree of hydrolysis may be determined by measuring the amount of free acetic acid via a pH titration according to methods known in the literature.

The graft copolymer may be characterized by a weight-average molecular weight of from about 2000 Daltons to about 500,000 Daltons, preferably from about 3000 Daltons to about 100,000 Daltons, more preferably 4,000 Daltons to about 50,000 Daltons, most preferably from about 10,000 to about 45,000 Daltons, even more preferably from about 20,000 to about 45,000 Daltons.

Preferably, the polyalkylene glycol of the graft base comprises a material selected from the group consisting of polyethylene glycol, polypropylene glycol, polybutylene glycol and mixtures thereof, more preferably said polyalkylene glycol comprises, or even is, polyethylene glycol.

The graft base may be characterized by a weight average molecular weight of from about 2000 to about 20,000 Daltons, or from about 2000 to about 15,000 Daltons, or from about 2000 to about 12,000 Daltons, or from about 4000 to about 12,000 Daltons, or from about 4000 to about 8000 Daltons.

The polyalkylene glycol of the graft copolymer may comprise polyethylene glycol ("PEG"), preferably a polyethylene glycol having a weight average molecular weight from about 2000 to about 20,000 Daltons, more preferably from about 2000 to about 12,000 Daltons.

The side chains may comprise vinyl acetate moieties (e.g., derived from vinyl acetate monomers) and vinylcaprolactam moieties (e.g., derived from vinylcaprolactam moieties). The vinyl acetate moieties and the vinycaprolactam moieties may be present in the side chains as "block chains", or as alternating moieties, for example randomly alternating.

The vinyl acetate moieties and vinylcaprolactam moieties may be present in the graft copolymer in a weight ratio of from about 1:10 to about 10:1, more preferably 5:1 to 1:5. The graft copolymer may be characterized by a weight ratio of the sum of the vinyl acetate moieties and vinylcaprolactam moieties to the polyalkylene glycol (e.g., side chains: graft base) that is from about 1:2 to about 10:1.

The graft copolymer may be obtainable from: (i) about 50 to 60 wt % N-vinylcaprolactam, (ii) about 25 to 35 wt % vinyl acetate, and (iii) about 10 to 20 wt % of the polyalkylene glycol, preferably polyethylene glycol; it may be that the sum of components i), ii), and iii) is equal to about 100 wt %.

The graft copolymer may comprise about 13 wt % polyethylene glycol having MW 6000, about 57 wt % N-vinylcaprolactam, and about 30 wt % vinyl acetate, where the wt % is by weight of the graft copolymer, preferably where the graft copolymer has a molecular weight of about 44,000 Daltons. It is believed that such graft copolymers include those sold as SOLUPLUS™ (ex BASF SE), as described in US2018/03056. The measured molecular weight, as determined by gel permeation chromatography, may appear higher, for example 90,000 to 140,000 Daltons.

The graft copolymer may be characterized by a hydrodynamic diameter of from about 10 nanometers to about 100 nanometers, more preferably from about 15 nanometers to about 80 nanometers, most preferably from about 20 nanometers to about 60 nanometers.

The graft copolymer may be characterized by a surface energy of from about 20 to about 90 mJ/m$^2$, preferably from about 20 to about 75 mJ/m$^2$, more preferably from about 20 to about 50 mJ/m$^2$. The test method to determine surface energy may be found in US2018/0071201 to The Procter & Gamble Company, paragraphs [0174]-[0176], incorporated herein by reference.

The graft copolymer may be considered a self-assembling graft copolymer. In the present disclosure, by "self-assembling," it is meant more than one polymer come together to make a particle through dispersion forces in a particular matrix, such as a detergent matrix, without requiring cross-linking or other reactions or additives.

The graft copolymers according to the present disclosure may be produced by free-radically initiated polymerization, for example in non-aqueous organic solvents or in mixed non-aqueous/aqueous solvents. Suitable production methods are described, for example, in WO2007/051743 and WO2009/013202.

b. Benefit Agent

The particles of the present disclosure comprise one or more benefit agents. As described above, it is believed that the benefit agents become embedded and/or encapsulated in the graft copolymers when the particles are formed. The particle formation can thus lead to improved stability, delivery, and/or performance of the benefit agent on a target surface, such as a fabric or hard surface. For example, such embedding and/or encapsulation of a benefit agent may prevent degradation of the benefit agent and/or undesirable interactions with other components of the liquid consumer product.

The compositions of the present disclosure may include the benefit agent and/or particles containing the benefit at a level at which the benefit agent provides its intended benefit when the composition is used as intended. For example, the benefit agent of the particles may be present at a level of from about 0.05% to about 10%, or from about 0.05% to about 5%, or from about 0.1% to about 4%, by weight of the composition.

The benefit agent may be selected from the group consisting of perfume raw materials, silicone oils, waxes, hydrocarbons, higher fatty acids, essential oils, lipids, skin coolants, vitamins, sunscreens, antioxidants, glycerine, catalysts, bleach particles, silicon dioxide particles, malodor reducing agents, odor-controlling materials, chelating agents, antistatic agents, softening agents, insect and moth repelling agents, colorants, antioxidants, chelants, bodying agents, drape and form control agents, smoothness agents, wrinkle control agents, sanitization agents, disinfecting agents, germ control agents, mold control agents, mildew control agents, antiviral agents, drying agents, stain resistance agents, soil release agents, fabric refreshing agents and freshness extending agents, chlorine bleach odor control agents, dye fixatives, dye transfer inhibitors, color maintenance agents, optical brighteners, color restoration/rejuvenation agents, anti-fading agents, whiteness enhancers, anti-abrasion agents, wear resistance agents, fabric integrity agents, anti-wear agents, anti-pilling agents, defoamers, anti-foaming agents, UV protection agents for fabrics and skin, sun fade inhibitors, anti-allergenic agents, enzymes, water proofing agents, fabric comfort agents, shrinkage resistance agents, stretch resistance agents, stretch recovery agents, skin care agents, glycerin, natural actives, aloe vera, vitamin E, shea butter, cocoa butter, brighteners, antibacterial actives, antiperspirant actives, cationic polymers, dyes, hueing dyes, skin heath agents, skin restoration agents, anti skin aging agents, facial contrast agents, anti dandruff agents, skin lightening agents, anti-acne agents, emollients, non-steroidal anti-inflammatory agents, topical anaesthetics, artificial tanning agents, anti-microbial and anti-fungal actives, skin soothing agents, skin barrier repair agents, anti-skin atrophy actives, lipids, sebum inhibitors, sebum inhibitors, skin sensates, protease inhibitors, anti-itch agents, desquamation enzyme enhancers, anti-glycation agents, and mixtures thereof. Particularly preferred benefit agents for the particles include perfume raw materials, enzymes, anti-microbial actives, anti-fungal actives, or mixtures thereof.

The benefit agent of the particles may include perfume raw materials. The term "perfume raw material" (or "PRM") as used herein refers to compounds having a molecular weight of at least about 100 g/mol and which are useful in imparting an odor, fragrance, essence, or scent, either alone or with other perfume raw materials. Typical PRMs comprise inter alia alcohols, ketones, aldehydes, esters, ethers, nitrites, and alkenes, such as terpene. A listing of common PRMs can be found in various reference sources, for example, "Perfume and Flavor Chemicals", Vols. I and II; Steffen Arctander Allured Pub. Co. (1994) and "Perfumes: Art, Science and Technology", Miller, P. M. and Lamparsky, D., Blackie Academic and Professional (1994).

Suitable perfume raw materials may include materials such as geraniol, linalool, linalyl acetate, pyranol, geranyl acetate, anisaldehyde, citral, citronellal, lysmeral, citronellol, rose oxide, tetrahydrolinalool, hydroxycitronellal, betaionone, menthol, cinnamaldehyde, anethole, vanillin, ethyl vanillin, eugenol, cinnamon oil, carvone, piperonal, and mixtures thereof. The perfume raw materials may include naturally derived materials, such as essential oils. The perfume raw materials may include aldehydes, preferably linear aldehydes, more preferably a linear aldehyde selected from decanal, undecanal, methyl nonyl acetaldehyde, adoxal, hexyl cinnamic aldehyde, or mixtures thereof.

The PRMs may be characterized by their boiling points (B.P.) measured at the normal pressure (760 mm Hg), and their octanol/water partitioning coefficient (P), which may be described in terms of log P, determined according to the test method below. Based on these characteristics, the PRMs may be categorized as Quadrant I, Quadrant II, Quadrant III, or Quadrant IV perfumes, as described in more detail below. A perfume having a variety of PRMs from different quadrants may be desirable, for example, to provide fragrance benefits at different touchpoints during normal usage.

The perfume raw materials may comprise a perfume raw material selected from the group consisting of perfume raw materials having a boiling point (B.P.) lower than about 250° C. and a Log P lower than about 3, perfume raw materials having a B.P. of greater than about 250° C. and a Log P of greater than about 3, perfume raw materials having a B.P. of greater than about 250° C. and a Log P lower than about 3, perfume raw materials having a B.P. lower than about 250° C. and a Log P greater than about 3 and mixtures thereof. Perfume raw materials having a boiling point B.P. lower than about 250° C. and a Log P lower than about 3 are known as Quadrant I perfume raw materials. Quadrant 1 perfume raw materials are preferably limited to less than 30% of the perfume composition. Perfume raw materials having a B.P. of greater than about 250° C. and a Log P of greater than about 3 are known as Quadrant IV perfume raw materials, perfume raw materials having a B.P. of greater than about 250° C. and a Log P lower than about 3 are known as Quadrant II perfume raw materials, perfume raw materials having a B.P. lower than about 250° C. and a Log P greater than about 3 are known as a Quadrant III perfume raw materials. Suitable Quadrant I, II, III and IV perfume raw materials are disclosed in U.S. Pat. No. 6,869,923 B1.

The particles of the present disclosure may be particularly useful for helping to effectively solubilize certain perfume raw materials in aqueous consumer product compositions, especially those that are relatively low in surfactant, thereby avoiding emulsifiers or other processing steps. In particular, the delivery particles of the present disclosure are useful when the benefit agent of the particles contain hydrophobic perfume raw materials. The hydrophobic perfume raw materials may be characterized by a relatively high log P value, for example a log P of greater than about 3.0, and may include what is described above as Quadrant III PRMs, Quadrant IV PRMs, or mixtures thereof. The benefit agent of the particles may comprise at least about 50%, or at least about 60%, or at least about 70%, or at least about 80%, or at least about 90%, or about 100%, by weight of the benefit agent, of Quadrant III PRMs, Quadrant IV PRMs, or mixtures thereof. Compositions that comprise such levels of Quadrant III and/or IV PRMs as the benefit agent of the particles may be aqueous and comprise at least 60%, or at least 70%, or at least 80%, or at least 90%, or at least 95%, or at least 97%, by weight of the composition, of water, and/or less than 10%, or less than 5%, or less than 3%, surfactant.

Non-limiting examples of Quadrant III PRMs include iso-bornyl acetate, carvacrol, alpha-citronellol, paracymene, dihydro myrcenol, geranyl acetate, d-limonene, linalyl acetate, vertenex, and mixtures thereof.

Non-limiting examples of Quadrant IV (or enduring) PRMs include allyl cyclohexane propionate, ambrettolide, amyl benzoate, amyl cinnamate, amyl cinnamic aldehyde, amyl cinnamic aldehyde dimethyl acetal, iso-amyl salicylate, hydroxycitronellal-methyl anthranilate (known as Aurantiol®), benzophenone, benzyl salicylate, para-tert-butyl cyclohexyl acetate, iso-butyl quinoline, beta-caryophyllene, cadinene, cedrol, cedryl acetate, cedryl formate, cinnamyl cinnamate, cyclohexyl salicylate, cyclamen aldehyde, dihydro isojasmonate, diphenyl methane, diphenyl oxide, dodecalactone, 1-(1,2,3,4,5,6,7,8-octahydro-2,3,8,8-tetramethyl-2-naphthalenyl)-ethanone (known as iso E Super®), ethylene brassylate, methyl phenyl glycidate, ethyl undecylenate, 15-hydroxypentadecanoic acid lactone (known as Exaltolide®), 1,3,4,6,7,8-hexahydro-4,6,6,7,8,8-hexamethyl-cyclopenta-gamma-2-benzopyran (known as Galaxolide®), geranyl anthranilate, geranyl phenyl acetate, hexadecanolide, hexenyl salicylate, hexyl cinnamic aldehyde, hexyl salicylate, alpha-irone, gamma-ionone, gamma-n-methyl ionone, para-tertiary-butyl-alpha-methyl hydrocinnamic aldehyde (known as Lilial®), lilial (p-t-bucinal)®, linalyl benzoate, 2-methoxy naphthalene, methyl dihydrojasmone, musk indanone, musk ketone, musk tibetine, myristicin, oxahexadecanolide-10, oxahexadecanolide-11, patchouli alcohol, 5-acetyl-1,1,2,3,3,6-hexamethylindan (known as Phantolide®), phenyl ethyl benzoate, phenylethylphenylacetate, phenyl heptanol, phenyl hexanol, alpha-santalol, delta-undecalactone, gamma-undecalactone, vetiveryl acetate, yara-yara, ylangene, and mixtures thereof.

The benefit agent of the particles may include enzymes. The enzymes may be selected to provide a benefit to a target surface, such as a cleaning benefit or a care/conditioning benefit.

Suitable enzymes may include, but are not limited to, hemicellulases, peroxidases, proteases, cellulases, xylanases, lipases, phospholipases, esterases, cutinases, pectinases, mannanases, pectate lyases, keratinases, reductases, oxidases, nucleases (include DNase and/or RNase), phenoloxidases, lipoxygenases, ligninases, pullulanases, tannases, pentosanases, malanases, ß-glucanases, arabinosidases, hyaluronidase, chondroitinase, laccase, amylases, or mixtures thereof. The benefit agent may comprise a mixture of enzymes, e.g. an enzyme cocktail that comprises protease, lipase, and amylase.

Particularly preferred enzymes may include lipase, amylase, protease, mannanase, cellulase, pectinase, and mixtures thereof. The enzyme may include lipase. It may be particularly preferred to provide lipase as a particle according to the present disclosure, as it is believed that doing so improves the stability of the lipase, particularly in aqueous compositions.

The enzymes may be of any suitable origin, such as vegetable, animal, bacterial, fungal (including yeast) origin or mixtures thereof, preferably bacterial and/or fungal.

Other factors influencing enzyme selection may include factors such as pH-activity and/or stability optima, thermostability, and stability to active detergents, builders, and the like.

The enzymes of the particles may be present at levels from about 0.00001% to about 2%, from about 0.0001% to about 1% or even from about 0.001% to about 0.5% enzyme protein, by weight of the composition.

When enzymes are present as a benefit agent of the particles according to the present disclosure, an enzyme stabilizing system may also be present. The enzyme stabilizing system may be present in the particles, in the liquid matrix of liquid consumer product composition (e.g., outside of the particles), or both. Such stabilizing systems can, for example, comprise calcium ion, boric acid, propylene glycol, short chain carboxylic acids, boronic acids, chlorine bleach scavengers and mixtures thereof, and may be selected/designed to address different stabilization problems depending on the type and physical form of the liquid consumer product composition.

The benefit agent of the particles may include anti-microbial agents, anti-fungal agents, or mixtures thereof, which may include methylglyoxal.

Water

The liquid compositions of the present disclosure may comprise water, preferably free water. The amount of free water is determined according to the test method section below.

The liquid consumer product compositions according to the present disclosure may comprise from about 1% to about 99%, or 10% to 99%, or from about 10% to about 96%, or from about 12% to about 90%, or from about 20% to about 80%, or from about 40% to about 80%, by weight of the composition, of water, preferably free water.

The liquid consumer product compositions of the present disclosure may contain relatively high amounts of water, preferably free water, such as greater than 50%, or greater than 60%, or greater than 70%, or greater than 80%, or greater than 90%, water, preferably free water. In particular, liquid compositions such as heavy-duty laundry detergents, liquid fabric conditioners (e.g., softeners or enhancers), and liquid hard surface cleaners may advantageously be formulated with high levels of water, for example to enhance flowability or dispersibility.

The compositions of the present disclosure may comprise less than 50 wt %, or less than 40 wt %, or less than 30 wt %, or less than 20 wt %, or less than 15 wt %, or less than 12 wt %, or less than 10 wt %, by weight of the composition, of water, preferably free water.

The liquid compositions of the present disclosure may be substantially non-aqueous, and may comprise less than 10 wt %, or less than 5 wt %, or less than 3 wt %, or less than 1 wt %, or less than 0.1 wt %, or even 0 wt %, by weight of the composition, of water, preferably free water.

The free water level may depend on the form and/or intended use of the composition. For example, when the composition is in the form of a unit dose composition (for example, a liquid composition encapsulated by a water-soluble film), the water, preferably free water, may be present at a level of from about 1% to about 20%, or from about 5% to about 15%; when the composition is in the form of a compact liquid laundry detergent, the water, preferably free water, may be present at a level of from about 10% to about 50%, or from about 20% to about 40%.

Adjunct Ingredients

The compositions of the present disclosure may include other adjunct ingredients. The adjuncts may be suitable for delivering a treatment benefit to a target surface, such as a fabric or other textile. Adjuncts ingredients, as used herein, may also include agents that facilitate chemical or physical stability in the treatment compositions, such as buffers, structurants/thickeners, and/or carriers.

The adjunct ingredient(s) may be present in the composition at levels suitable for the intended use of the composition. Typical usage levels range from as low as 0.001% by weight of composition for adjuncts such as optical brighteners to 50% by weight of composition for builders.

The adjunct may include an amine, a surfactant system, a water-binding agent, a sulfite, fatty acids and/or salts thereof, enzymes, encapsulated benefit agents, soil release polymers, hueing agents, builders, chelating agents, dye transfer inhibiting agents, dispersants, enzyme stabilizers, catalytic materials, bleaching agents, bleach catalysts, bleach activators, polymeric dispersing agents, soil removal/anti-redeposition agents, polymeric dispersing agents, polymeric grease cleaning agents, brighteners, suds suppressors, dyes, hueing agents, free perfume, structure elasticizing agents, fabric softeners, carriers, fillers, hydrotropes, organic solvents, anti-microbial agents and/or preservatives, neutralizers and/or pH adjusting agents, processing aids, fillers, rheology modifiers or structurants, opacifiers, pearlescent agents, pigments, anti-corrosion and/or anti-tarnishing agents, and mixtures thereof. The compositions of the present disclosure may include, among other things, an amine, a surfactant system, a conditioning agent, a water-binding agent, a sulfite, a structurant, organic solvent, free perfume, or mixtures thereof. Several of these adjuncts are described in more detail below.

The consumer product adjunct may comprise a surfactant system, conditioning actives, or combinations thereof. Preferably, the surfactant system comprises anionic surfactant, nonionic surfactant, cationic surfactant, and/or zwitterionic surfactant. Preferably, the fabric softening agents comprise a quaternary ammonium compound, silicone compounds, or both.

Liquid consumer product compositions according to the present disclosure may include a surfactant system. The surfactant system may consist of one type of surfactant. The surfactant system may include more than one surfactant.

The compositions of the present disclosure may include from about 20% to about 75%, or from about 25% to about 70%, or from about 30% to about 50%, by weight of the composition, of a surfactant system. Compositions of the present disclosure may include less than 20%, or less than 10%, or less than 5%, or less than 3%, by weight of the composition, of a surfactant system.

The surfactant system may include anionic surfactant, nonionic surfactant, zwitterionic surfactant, cationic surfactant, amphoteric surfactant, or combinations thereof. The surfactant system may include linear alkyl benzene sulfonate, alkyl ethoxylated sulfate, alkyl sulfate, nonionic surfactant such as ethoxylated alcohol, amine oxide, or mixtures thereof. The surfactants may be, at least in part, derived from natural sources, such as natural feedstock alcohols.

Suitable anionic surfactants may include any conventional anionic surfactant. This may include a sulfate detersive surfactant, for e.g., alkoxylated and/or non-alkoxylated alkyl sulfate materials, and/or sulfonic detersive surfactants, e.g., alkyl benzene sulfonates. The anionic surfactants may be linear, branched, or combinations thereof. Preferred surfactants include linear alkyl benzene sulfonate (LAS), alkyl ethoxylated sulfate (AES) including sodium laureth sulfate (SLES), alkyl sulfates (AS) including sodium lauryl sulfate (SLS), or mixtures thereof. Other suitable anionic surfactants include branched modified alkyl benzene sulfonates (MLAS), methyl ester sulfonates (MES), and/or alkyl ethoxylated carboxylates (AEC). The anionic surfactants may be present in acid form, salt form, or mixtures thereof. The anionic surfactants may be neutralized, in part or in whole, for example, by an alkali metal (e.g., sodium) or an amine (e.g., monoethanolamine)

The surfactant system may include nonionic surfactant. Suitable nonionic surfactants include alkoxylated fatty alcohols, such as ethoxylated fatty alcohols. Other suitable nonionic surfactants include alkoxylated alkyl phenols, alkyl phenol condensates, mid-chain branched alcohols, mid-chain branched alkyl alkoxylates, alkylpolysaccharides (e.g., alkylpolyglycosides), polyhydroxy fatty acid amides, ether capped poly(oxyalkylated) alcohol surfactants, and mixtures thereof. The alkoxylate units may be ethyleneoxy units, propyleneoxy units, or mixtures thereof. The nonionic surfactants may be linear, branched (e.g., mid-chain branched), or a combination thereof. Specific nonionic surfactants may include alcohols having an average of from about 12 to about 16 carbons, and an average of from about 3 to about 9 ethoxy groups, such as C12-C14 EO7 nonionic surfactant.

Suitable zwitterionic surfactants may include any conventional zwitterionic surfactant, such as betaines, including alkyl dimethyl betaine and cocodimethyl amidopropyl betaine, $C_8$ to $C_{18}$ (for example from $C_{12}$ to $C_{18}$) amine oxides (e.g., $C_{12\text{-}14}$ dimethyl amine oxide), and/or sulfo and hydroxy betaines, such as N-alkyl-N,N-dimethylammino-1-propane sulfonate where the alkyl group can be $C_8$ to $C_{18}$, or from $C_{10}$ to $C_{14}$. The zwitterionic surfactant may include amine oxide.

It is believed that compositions having certain surfactant types at certain levels, for example nonionic surfactant such as ethoxylated alcohol, and/or anionic surfactant such as linear alkyl benzene sulphonate (LAS), are particularly likely to facilitate the self-assembly of particles. For example, the compositions of the present disclosure may include, by weight of the composition: from about 2%, to about 15%, or from about 4% to about 12%, of nonionic surfactant, such as an ethoxylated alcohol; and/or from about 0% (including none) to about 8%, or from about 1% to about 6%, of LAS. The total amount of nonionic surfactant (e.g., ethoxylated alcohol) and LAS may be from about 4% to about 15%, or from about 6% to about 12%, by weight of the composition. The weight ratio of nonionic surfactant (e.g., ethoxylated alcohol) to LAS may be from about 1:3 to about 1:0, or from about 1:1 to about 15:1.

The compositions of the present disclosure may include a conditioning active. Compositions that contain conditioning actives may provide softness, anti-wrinkle, anti-static, conditioning, anti-stretch, color, and/or appearance benefits. Conditioning actives suitable for compositions of the present disclosure may include quaternary ammonium ester compounds, silicones, non-ester quaternary ammonium compounds, amines, fatty esters, sucrose esters, silicones, dispersible polyolefins, polysaccharides, fatty acids, softening or conditioning oils, polymer latexes, or combinations thereof.

Conditioning actives may be present at a level of from about 1% to about 99%, by weight of the composition. The composition may include from about 1%, or from about 2%, or from about 3%, to about 99%, or to about 75%, or to about 50%, or to about 40%, or to about 35%, or to about 30%, or to about 25%, or to about 20%, or to about 15%, or to about 10%, by weight of the composition, of conditioning active. The composition may include from about 5% to about 30%, by weight of the composition, of conditioning active.

A water-binding agent can be added to a liquid composition to lower its free water content. The water-binding agents may comprise organic acids, salts of organic acids, humectants, desiccants, natural sugar substitutes, artificial sugar substitutes, hydrogels, or mixtures thereof.

Liquid consumer product compositions according to the present disclosure may include an external structurant. External structurants can provide physical stability to liquid compositions according to the present disclosure, for example by helping to suspend the delivery particles. External structurants may include non-polymeric crystalline, hydroxy-functional structurants and/or polymeric structurants.

Non-polymeric crystalline, hydroxyl functional structurants may comprise a crystallizable glyceride, which may be pre-emulsified to aid dispersion into the final detergent composition. Suitable crystallizable glycerides include hydrogenated castor oil or "HCO" or derivatives thereof, provided that it is capable of crystallizing in the liquid detergent composition.

Polymeric structurants may include naturally derived structurants and/or synthetic structurants. Naturally derived polymeric structurants include: hydroxyethyl cellulose, hydrophobically modified hydroxyethyl cellulose, carboxymethyl cellulose, polysaccharide derivatives and mixtures thereof. Suitable polysaccharide derivatives include: pectine, alginate, arabinogalactan (gum Arabic), carrageenan, gellan gum, xanthan gum, guar gum and mixtures thereof. The structurant may comprise cellulosic fibers, for example in the form of microfibrillated cellulose. Cellulose may be derived from bacterial, wood, or other plants such as fruit or sugar beet.

Synthetic polymeric structurants include: polycarboxylates, polyacrylates, hydrophobically modified ethoxylated urethanes, hydrophobically modified non-ionic polyols and mixtures thereof. The polycarboxylate polymer may be a polyacrylate, polymethacrylate or mixtures thereof. The polyacrylate may be a copolymer of unsaturated mono- or di-carbonic acid and $C_1$-$C_{30}$ alkyl ester of the (meth)acrylic acid. Such copolymers are available from Lubrizol Corp. under the tradename Carbopol® Aqua 30.

The compositions of the present disclosure may include solvent, preferably organic solvent, such as a non-amino-functional organic solvent. Suitable organic solvents may include glycerol, ethylene glycol, 1,3 propanediol, 1,2 propanediol, tetramethylene glycol, pentamethylene glycol, hexamethylene glycol, 2,3-butane diol, 1,3 butanediol, diethylene glycol, triethylene glycol, polyethylene glycol, glycerol formal dipropylene glycol, polypropylene glycol, dipropylene glycol n-butyl ether, and mixtures thereof. Organic solvents can provide physical stability benefits, particularly in compact formulations having relatively low water levels. The compositions of the present disclosure may include from about 5% to about 80%, or from about 10% to about 50%, by weight of the composition, of organic solvent.

The compositions of the present disclosure may include additional aesthetic agents, such as those selected from dyes, opacifiers, pearlescent agents, or mixtures thereof.

When the consumer product composition is in the form of a unit dose article, such as a pouch or a sachet, the composition may be encapsulated by a water-soluble film. A water-soluble unit dose article may comprise at least one water-soluble film shaped such that the unit-dose article comprises at least one internal compartment surrounded by the water-soluble film. The at least one compartment comprises the detergent composition.

The unit dose article may comprise more than one compartment, even at least two compartments, or even at least three compartments, or even at least four compartments, or even at least five compartments. The compartments may be arranged in superposed orientation, i.e. one positioned on top of the other. Alternatively, the compartments may be positioned in a side-by-side orientation, i.e. one orientated next to the other. The compartments may even be orientated in a "tire and rim" arrangement, i.e. a first compartment is positioned next to a second compartment, but the first compartment at least partially surrounds the second compartment, but does not completely enclose the second compartment. Alternatively, one compartment may be completely enclosed within another compartment. When one compartment comprises a liquid composition according to the present disclosure, another compartment may comprise a solid, a liquid, or a mixture thereof.

The film of the present invention may be soluble or dispersible in water (e.g., at 20° C.). Preferred film materials include polymeric materials. The film material can, for example, be obtained by casting, blow-moulding, extrusion or blown extrusion of the polymeric material, as known in the art. Preferably, the water-soluble film comprises polyvinyl alcohol polymer or copolymer, preferably a blend of polyvinylalcohol polymers and/or polyvinylalcohol copolymers, preferably selected from sulphonated and carboxylated anionic polyvinylalcohol copolymers especially carboxylated anionic polyvinylalcohol copolymers, most preferably a blend of a polyvinylalcohol homopolymer and a carboxylated anionic polyvinylalcohol copolymer. Suitable films include those supplied by MonoSol, LLC (Indiana) under the trade references M8630, M8900, M8779, and/or M8310. The film may comprise an aversive agent, for example a bittering agent. Prior to be being formed into a unit dose article, the water-soluble film preferably has a thickness of from 20 to 150 microns, preferably 35 to 125 microns, even more preferably 50 to 110 microns, most preferably about 76 microns.

Process of Making

The present disclosure also relates to processes for making feedstock compositions and/or liquid consumer product compositions.

For example, the present disclosure relates to a method of making a liquid consumer product composition, the method comprising the steps of: providing a feedstock composition, preferably a liquid feedstock composition, comprising a benefit agent and a graft copolymer, the graft copolymer comprising a polyalkylene glycol as a graft base and one or more side chains that comprise vinyl acetate moieties and N-vinylcaprolactam moieties; combining the feedstock composition with a base composition, the base composition comprising a consumer product adjunct, wherein the resulting liquid consumer product composition comprises delivery particles that comprise the benefit agent and the graft copolymer.

The feedstock composition may be at a temperature above ambient conditions, preferably above about 35° C., more preferably above about 40° C., when the feedstock composition is combined with the base composition. It is believed that elevating the temperature of the feedstock composition can help the processability, such as the pouring and/or mixing, of the feedstock composition into the base composition.

The graft copolymer may be characterized by a melting point. The step of providing the liquid feedstock composition may include combining the graft copolymer and the benefit agent when the graft copolymer is at a temperature greater than the melting point of the graft copolymer.

The feedstock composition, the base composition, or both may comprise water, preferably at least 40 wt % water. The feedstock composition may be substantially free of water. The feedstock composition may be combined or diluted with water prior to being combined with the base composition.

The weight ratio of the benefit agent to the graft copolymer in the feedstock composition may be from about 10:90 to about 90:10, or from about 20:80 to about 80:20, or from about 30:70 to about 70:30, or from about 40:60 to about 60:40, or about 50:50. The feedstock composition may comprise at least about 10%, or at least about 20%, or at least about 30%, or at least about 40%, or at least about 50%, by weight of the feedstock composition, of the benefit agent, such as perfume raw materials. The feedstock composition may comprise at least about 10%, or at least about 20%, or at least about 30%, or at least about 40%, or at least about 50%, by weight of the feedstock composition, of the graft copolymer.

The method may further comprise providing the liquid consumer product composition to a container. The container may be water-insoluble, such as a plastic bottle or tub. The container may be water-soluble, such as a pouch formed from water-soluble film (e.g., PVOH film).

The process may include combining a graft copolymer according to the present disclosure with a benefit agent, such as perfume, according to the present disclosure and mixing until relatively homogenous. It is believed that by making such a feedstock composition in which the benefit agent (e.g., perfume) and polymer are well-dispersed, particles can form via self-assembly when the feedstock composition is added to a base composition that includes adjunct material(s). In contrast, it is believed that that separately adding graft co-polymer and benefit agents such as perfume to a consumer product composition does not result in the formation of benefit agent delivery particles which comprise graft co-polymer and benefit agent.

The step of premixing the graft copolymer and benefit agent (e.g., perfume) in a feedstock composition is preferably achieved by mixing the graft co-polymer and perfume in a mixing device at a rate of from about 500 to about 3000 rpm, preferably from about 600 to about 2500 rpm, and more preferably about 2500 rpm.

The process of combining the graft copolymer and the benefit agent (e.g., perfume) may further include heating the graft copolymer to a temperature above a melting point of the graft copolymer. The process may include heating the graft co-polymer to at least 45° C. Such heating can facilitate easier mixing.

Solvents, such as aqueous and/or organic solvents, may be added to the polymer if it is initially too viscous to allow for efficient mixing. Water may be utilized in the present processes and resulting compositions (including feedstock compositions and/or consumer product compositions) at levels of less than about 98%, preferably less than about 96%, preferably less than about 90% by weight of the composition, of water. Water can be utilized at levels of from about 1% to about 98%, preferably from about 5% to about 95%, preferably from about 5% to about 90%, preferably from about 5% to about 85%, preferably from about 5% to about 70%, by weight of the composition, of water.

The present disclosure further relates to a liquid consumer product composition, such as those described herein, obtainable by the methods described herein.

Process of Treating a Surface

The present disclosure also relates to a process of treating a surface, such as a fabric, hair, and/or skin. The process may include the step of contacting a surface with a compact liquid detergent composition according to the present disclosure.

The contacting step may occur in the presence of water. As described above, it is believed that in the presence of water, the perfume raw materials are released from the graft copolymers. The processes of the present disclosure may include diluting the compact liquid detergent composition with water to form a treatment liquor, which may contact the surface to be treated. The compact liquid detergent composition may be diluted from 100-fold to 1000-fold, or from 200-fold to 900-fold, or from 300-fold to 800-fold, by water.

The contacting step may occur in the drum of an automatic washing machine. The contacting step may occur as a pretreatment step.

Combinations

Specifically contemplated combinations of the disclosure are herein described in the following lettered paragraphs. These combinations are intended to be illustrative in nature and are not intended to be limiting.

A. A liquid consumer product composition comprising delivery particles and a consumer product adjunct, the delivery particles comprising a graft copolymer and a benefit agent, the graft copolymer comprising a polyalkylene glycol as a graft base and one or more side chains, the side chains comprising vinyl acetate moieties and N-vinylcaprolactam moieties.

B. The liquid consumer product composition according to paragraph A, wherein the delivery particles are characterized by a number-average diameter of from about 0.5 microns to about 5000 microns, preferably from about 0.5 microns to about 1000 microns, more preferably from about 0.5 microns to about 250 microns, most preferably from about 0.5 microns to about 60 microns.

C. The liquid consumer product composition according to either of paragraphs A or B, wherein the composition comprises from about 1% to about 99%, or 10% to 99%, or from about 10% to about 96%, or from about 12% to about 90%, or from about 20% to about 80%, or from about 40% to about 80%, by weight of the composition, of free water.

D. The liquid consumer product composition according to any of paragraphs A-C, wherein the graft copolymer is characterized by a weight average molecular weight from about 2000 Daltons to about 500,000 Daltons, preferably from about 3000 Daltons to about 100,000 Daltons, more preferably 4,000 Daltons to about 50,000 Daltons, most preferably from about 10,000 to about 45,000 Daltons.

E. The liquid consumer product composition according to any of paragraphs A-D, wherein the graft base is characterized by a weight average molecular weight of from about 2000 to about 15,000 Daltons.

F. The liquid consumer product composition according to any of paragraphs A-E, wherein the polyalkylene glycol of the graft copolymer comprises polyethylene glycol ("PEG"), preferably a polyethylene glycol having a weight average molecular weight from about 2000 to about 20,000 Daltons, more preferably from about 2000 to about 12,000 Daltons.

G. The liquid consumer product composition according to any of paragraphs A-F, wherein the weight ratio of vinyl acetate moieties to vinylcaprolactam moieties is from about 1:10 to about 10:1, more preferably 5:1 to 1:5.

H. The liquid consumer product composition according to any of paragraphs A-G, wherein the weight ratio of the sum of the vinyl acetate moieties and vinylcaprolactam moieties to the polyalkylene glycol (e.g., side chains:graft base) is from about 1:2 to about 10:1.

I. The liquid consumer product composition according to any of paragraphs A-H, wherein the graft copolymer is obtainable from: i) 50 to 60 wt % N-vinylcaprolactam, ii) 25 to 35 wt % vinyl acetate, and iii) 10 to 20 wt % of the polyalkylene glycol, preferably polyethylene glycol, with the proviso that the sum of components i), ii), and iii) is equal to about 100 wt %.

J. The liquid consumer product composition according to any of paragraphs A-I, wherein the graft copolymer comprises about 13 wt % polyethylene glycol having MW 6000, about 57% N-vinylcaprolactam, and about 30 wt % vinyl acetate, preferably wherein the graft copolymer has a weight average molecular weight of about 44,000 Daltons.

K. The liquid consumer product composition according to any of paragraphs A-J, wherein the benefit agent is present in an amount of from about 0.01% to about 5%, or from about 0.02% to about 5%, or from about 0.05% to about 4%, by weight of the composition.

L. The liquid consumer product composition according to any of paragraphs A-K, wherein the benefit agent is selected from the group consisting of perfume raw materials, silicone oils, waxes, hydrocarbons, higher fatty acids, essential oils, lipids, skin coolants, vitamins, sunscreens, antioxidants, glycerine, catalysts, bleach particles, silicon dioxide particles, malodor reducing agents, odor-controlling materials, chelating agents, antistatic agents, softening agents, insect and moth repelling agents, colorants, antioxidants, chelants, bodying agents, drape and form control agents, smoothness agents, wrinkle control agents, sanitization agents, disinfecting agents, germ control agents, mold control agents, mildew control agents, antiviral agents, drying agents, stain resistance agents, soil release agents, fabric refreshing agents and freshness extending agents, chlorine bleach odor control agents, dye fixatives, dye transfer inhibitors, color maintenance agents, optical brighteners, color restoration/rejuvenation agents, anti-fading agents, whiteness enhancers, anti-abrasion agents, wear resistance agents, fabric integrity agents, anti-wear agents, anti-pilling agents, defoamers, anti-foaming agents, UV protection agents for fabrics and skin, sun fade inhibitors, anti-allergenic agents, enzymes, water proofing agents, fabric comfort agents, shrinkage resistance agents, stretch resistance agents, stretch recovery agents, skin care agents, glycerin, natural actives, aloe vera, vitamin E, shea butter, cocoa butter, brighteners, antibacterial actives, antiperspirant actives, cationic polymers, dyes, hueing dyes, skin heath agents, skin restoration agents, anti skin aging agents, facial contrast agents, anti dandruff agents, skin lightening agents, anti-acne agents, emollients, non-steroidal anti-inflammatory agents, topical anaesthetics, artificial tanning agents, anti-microbial and anti-fungal actives, skin soothing agents, skin barrier repair agents, anti-skin atrophy actives, lipids, sebum inhibitors, sebum inhibitors, skin sensates, protease inhibitors, anti-itch agents, desquamation enzyme enhancers, anti-glycation agents, and mixtures thereof, preferably perfume raw materials, enzymes, anti-microbial actives, anti-fungal actives, or mixtures thereof, more preferably perfume raw materials.

M. The liquid consumer product composition according to any of paragraphs A-L, wherein the benefit agent comprises perfume raw materials, preferably perfume raw materials selected from Quadrant III perfume raw materials, Quadrant IV perfume raw materials, or mixtures thereof, more preferably wherein the liquid consumer product composition comprises at least 60%, or at least 70%, or at least 80%, or at least 90%, or at least 95%, by weight of the composition, of water, and/or less than 10%, or less than 5%, or less than 3%, surfactant.

N. The liquid consumer product composition according to any of paragraphs A-M, wherein the benefit agent comprises enzymes, preferably lipase, amylase, protease, mannanase, cellulase, pectinase, and mixtures thereof, more preferably lipase.

O. The liquid consumer product composition according to any of paragraphs A-N, wherein the consumer product composition is a fabric care composition, a hard surface cleaner composition, a dish care composition, a hair care composition, a body cleansing composition, or a mixture thereof, preferably wherein the fabric care composition is a fabric detergent composition, a fabric conditioning composition, or a mixture thereof.

P. The liquid consumer product composition according to any of paragraphs A-O, wherein the composition is encapsulated in a water-soluble film.

Q. The liquid consumer product composition according to any of paragraphs A-P, wherein the consumer product adjunct is selected from an amine, a surfactant system, a water-binding agent, a sulfite, fatty acids and/or salts thereof, enzymes, encapsulated benefit agents, soil release polymers, hueing agents, builders, chelating agents, dye transfer inhibiting agents, dispersants, enzyme stabilizers, catalytic materials, bleaching agents, bleach catalysts, bleach activators, polymeric dispersing agents, soil removal/anti-redeposition agents, polymeric dispersing agents, polymeric grease cleaning agents, brighteners, suds suppressors, dyes, hueing agents, free perfume, structure elasticizing agents, fabric softening agents, carriers, fillers, hydrotropes, organic solvents, anti-microbial agents and/or preservatives, neutralizers and/or pH adjusting agents, processing aids, fillers, rheology modifiers or structurants, opacifiers, pearlescent agents, pigments, anti-corrosion and/or anti-tarnishing agents, and mixtures thereof.

R. The liquid consumer product composition according to any of paragraphs A-Q, wherein consumer product adjunct comprises a surfactant system, fabric softeners, or combinations thereof, preferably wherein the surfactant system comprises anionic surfactant, nonionic surfactant, cationic surfactant, and/or zwitterionic surfactant, and/or preferably wherein the fabric softening agents comprise a quaternary ammonium compound, silicone compounds, or both.

S. A method of making a liquid consumer product composition, the method comprising the steps of: providing a liquid feedstock composition comprising a benefit agent and a graft copolymer, the graft copolymer comprising a polyalkylene glycol as a graft base and one or more side chains that comprise vinyl acetate moieties and N-vinylcaprolactam moieties; combining the feedstock composition with a base composition, the base composition comprising a consumer product adjunct, wherein the resulting liquid consumer product composition comprises delivery particles that comprise the benefit agent and the graft copolymer.

T. The method according to paragraph S, wherein the feedstock composition is at a temperature above ambient conditions, preferably above about 35° C., more preferably above about 40° C., when the feedstock composition is combined with the base composition.

U. The method according to either of paragraphs S or T, wherein the feedstock composition, the base composition, or both comprise at least 40 wt % water.

V. The method according to any of paragraphs S-U, wherein the graft copolymer is characterized by a melting point, and wherein the step of providing the liquid feedstock composition comprises combining the graft copolymer and the benefit agent at a temperature greater than the melting point of the graft copolymer.

W. A liquid consumer product composition obtainable by the method according to any of paragraphs S-V, preferably wherein the liquid consumer product composition is according to any of paragraphs A-R.

X. A process of treating a surface, the process comprising the step of contacting the surface with a liquid consumer product composition according to any of paragraphs A-R or W.

Test Methods

It is understood that the test methods that are disclosed in the Test Methods Section of the present application should be used to determine the respective values of the parameters of Applicant's invention as such invention is described and claimed herein.

1. Number-Weighted Average Diameter and Structure Test Method

Microscopy is used to measure the number-weighted average diameter (or simply "diameter" as used herein) of the co-polymer particles. Microscopy is also used to determine the structure of the particles via observing the frequency and the location of benefit agent regions in the particles. The microscopic measurement particle diameter may be conducted using any microscopic technique capable of imaging the external size of the particles in the sample. The microscopic determination of structure may be conducted using any microscopic technique capable of imaging the internal presence and location of the benefit agent regions in the particles. Suitable microscopy techniques may include but are not limited to: Scanning Electron Microscopy (SEM); Phase Contrast Microscopy; Differential Interference Contrast microscopy (DIC); Fluorescence Microscopy; and Confocal Laser Scanning Fluorescence Microscopy (CLSM). One of skill will understand that different and various sample preparation steps may be required for the different imaging techniques which may be suitable. In all cases, the number-weighted average diameter of the particles is calculated from the values obtained by microscopically observing and measuring the diameter of at least 30 randomly selected particles in a sample.

The structure of the particles is assessed by microscopically observing and determining the frequencies and locations of all observable benefit agent regions in at least 30 randomly selected particles in a sample. In the case of optical light microscopy techniques it is suitable to use a high magnification water-immersion objective lens such as a 63×/1.2 NA Water lens (Zeiss) to observe 0.5 mL of sample placed into a Chambered Coverglass such as Chambered #1.0 Borosilicate Coverglass System (such as from LabTek) and to dilute the sample as necessary to obtain unobstructed images of the particle diameter and structure. In the case of fluorescence microscopy and especially fluorescence confocal laser scanning microsopy (CLSM), the selective labeling of the polymers and the benefit agents with different fluorescent dyes can enable their separate detection via excitation with different wavelengths of light. For example, by labeling the polymer(s) with a red dye label such as Rhodamine isothiocyanate ($\lambda ex=561$ nm), and the benefit agents with a dye probe having a different excitation wavelength, for example such as Coumarin 6 ($\lambda ex=488$ nm), it is then possible to determine where the polymer and the benefit agents are located by means of different filters and detectors on the microscope. By using the overlay of images from the different detectors it is possible to identify the regions of co-localization, and observe the frequency and spatial location of the benefit agent regions relative to the particle and its polymer regions.

2. Free Water Content Test Method

Free water content (FWC) refers to the amount of freezable non-bound water with a temperature of fusion around 0° C. and is defined as:

$$FWC\ \% = \left(\frac{\Delta H_{f,sample} * m_{sample}}{\Delta H_{f,H_2O}}\right) / m_{sample} * 100$$

where $\Delta H_{f,sample}$ is the enthalpy of fusion of water in the sample in J/g, $m_{sample}$ is the weight of the sample in g, and $\Delta H_{f,H_2O}$ is the enthalpy of fusion of pure water in J/g.

1. Materials

Differential scanning calorimetry with refrigerated cooling system, such as DSC-Q2000 with DSC software Advantage for Q series version 5.4.0, and Analysis software such as Universal analysis 2000 version 4.5A (TA instruments), or equivalents.

Analytical balance (sensitivity 0.0001 g), such as Sartorius CP225 D.

DSC Steel pan, such as Perkin Elmer model: 0319-1525 (bottom) 0319-1526(cover) 0319-1535 (O-ring)

2. Procedure to Measure $\Delta H_{f,sample}$

1) Weight on the balance the Steel pan with its cover and the O-ring. Note the weight ($W_p$)
2) Assemble the O-ring with the cover
3) Weight on the balance the amount of sample (10-20 mg) added into the pan, note the weight ($W_{s+p}$)
4) Close the pan hermetically
5) Calculate $W_s=W_{s+p}-W_p$
6) Insert the pan in the DSC
7) Open the Nitrogen line (flow must be not below 50 ml/min)
8) Open the software TA instrument explorer
9) Turn on the cooler from the button control and then press "event on" on the software
10) The software is subdivided into three main parts. (Summary-procedure-notes). In summary you have to write the details of the sample (sample name, $W_p$, $W_s$) and the type of pan you are using, then select the directory to save the data and flag "pan mass". In the 'Procedure' panel by pressing 'Editor' you can write down the procedure needed for your samples. Here we report the procedure used to calculate the FWC.
Equilibrate at 5° C.
Data storage on
Ramp 0.5°/min to −80° C.
Mark the end of the cycle "0"
Ramp 0.5° C./min to 25° C.
Mark the end of the cycle "1"
In the 'notes' panel choose the appropriate calibration in this case (Steel pan 0.5° C./min)
11) Press 'apply' button to complete the run procedure and start from the main software panel.
12) Once the run is done it will be green flagged 3. Procedure to Analyze the Data
1) Open the data collected with the DSC, using the analysis software (Universal analysis 2000 version 4.5A)
2) Expand the region of interests (typically between −20 and +5° C.)
3) Click on "Integrate Peak Linear"
4) Double-click before and after the thermal peak to insert two cursors that determine the integration limits
5) Right-click in between the two cursors and click on "accept limits"
6) The software calculates $\Delta H_{f,sample}$ in J/g 4. Determination of $\Delta H_{f,H_2O}$ Instead of using the standard value of 333.55 J/g as $\Delta H_{f,H_2O}$, one can calculate $\Delta H_{f,H_2O}$ for the instrument used (the value should be comprised between 333.55±30 J/g).

Three samples of 1-2 mg of deionized water (such as MilliQ grade, 18.2 MΩ cm) each are precisely weighted in a DSC steel pan (take note of the precise weight) and placed in a DSC. All samples are analyzed using the same procedure used to determine $\Delta H_{f,sample}$ described. Once determined $\Delta H_{f,sample}$, $\Delta H_{f,H_2O}$, one can calculate the FWC.

3. Weight-Average Molecular Weight Test Method

Weight-average molecular weight values are determined using high performance liquid chromatography (HPLC) instrument system with a refractive index detector, such as the Waters Alliance 2695 system equipped with autosampler and Waters 2414 refractive index detector (Waters Inc., Milford, Mass., USA). Data storage and analysis are performed with Astra 6.1.6 software (Wyatt Technologies, Santa Barbara, Calif., USA). The chromatographic conditions used are as specified in the table below:

| Parameter | Conditions |
| --- | --- |
| Column Set | Guard Column - TSK Gel Guard HXL-H in-line with Three TOSOH columns: TSK Gel G4000HXL Catalog #0016137; TSK Gel G5000HXL Catalog #0016138; TSK Gel G6000HXL Catalog #0016139; |
| Mobile Phase | Tetrahydrofuran (THF) |
| Flow Rate | 1 mL/min |
| Column Temperature | 25° C. |
| Injection Volume | 100 µL |
| Detector Temperature | 35° C. |

In carrying out the calculations, the results are calibrated using a set of 12 polystyrene reference samples, such as the EasiVial PS-M set (Agilent Technologies, Santa Clara, Calif.) having known molecular weights ranging from 162 to 364,000 $M_p$ and using a second order fit. The molecular weight analyses are determined using a tetrahydrofuran (THF) mobile phase. The table below shows the molecular weights and the retention times of the polystyrene standards:

| Standard Number | Average Reported Mp | Retention Time (min) |
| --- | --- | --- |
| 1 | 364,000 | 21.75 |
| 2 | 195,300 | 23.02 |
| 3 | 110,500 | 24.18 |
| 4 | 49,010 | 25.78 |
| 5 | 30,230 | 26.61 |
| 6 | 12,980 | 27.90 |
| 7 | 7,640 | 28.60 |
| 8 | 2,970 | 29.71 |
| 9 | 1,150 | 30.79 |
| 10 | 855 | 31.10 |

-continued

| Standard Number | Average Reported Mp | Retention Time (min) |
|---|---|---|
| 11 | 370 | 31.91 |
| 12 | 162 | 32.95 |

4. Grafting and Ratio of Polyalkylene Glycol: Vinyl Acetate Moieties Test Methods The percent grafting is determined by 13C-NMR using a Bruker 600 MHz NMR. An inverse-gated 30° pulse sequence is used, with 16,000 scans and relaxation delay of 5 sec. Samples are prepared at 50 mg/ml in deuterated DMSO-d6 with addition of 0.79 mg/ml $Gd(NO_3)_3$ and 0.31 mg/ml Inositol as a Paramagnetic Relaxation Reagent. The ratio of the integration of the area between 76.75-77.5 ppm for the graft methine carbon and the integration of the area between 70.00-70.65 ppm for the PEG carbons is calculated and converted to a percent.

The weight percents for Polyalkylene Glycol: Vinyl Acetate Moieties are calculated by averaging the integration of the area of the NMR proton spectra between 1.35-2.07 ppm & 4.65-5.1 ppm for polyvinyl acetate and 3.38-3.58 ppm for Polyalkylene Glycol. The integrations are divided to find a molar ratio, and then multiplied by their respective molar mass to calculate the weight percents.

5. Method of Measuring Viscosity

Viscosity is measured using a HAAKE MARS from Thermo Scientific using a 60 mm 1° Cone and a gap size of 52 micrometers. The shear viscosity at 20 $s^{-1}$ can be obtained from a logarithmic shear rate sweep from 0.01 $s^{-1}$ to 1200 $s^{-1}$ at 21° C. The viscosity may be expressed as centipoise (cP).

6. Color Difference Determination ($\Delta E$)

To measure the color difference between two liquid compositions, a delta-E ($\Delta E$) value can be determined according to the following procedure.

Vis spectra for test samples and reference samples may be collected at desired time intervals, for example when prepared (fresh, or time=0) and/or after 28 days of storage.

To measure the color differences, turn on the UV/Vis spectrometer and open the instrument control software. Insert an empty cuvette in the sample location inside the instrument. Click on "Zero" and wait until the procedure is completed. Click on File/Setup. In the 'Scan' panel choose 700-400 nm scan range, 1 nm for data interval, and 0.1 s for Average time, then press "OK". Press "START" in the software main window. Generate directories for both Methods and Data and then press "OK". Wait until the spectrum is collected. Save spectra for samples and references in the .CSV format. Click on File/Open Data and select the sample spectrum. Click on File/Setup. In the 'Illuminants and Observer' setup choose "CIE D65" as Illuminant and "2 degrees" as Observer. In the 'Color Space' panel choose "CIE Lab" as color space. In the 'Color Differences' panel choose DeltaE as color difference, then click on "Standard File" and then browse and select the reference spectrum (either polymer or perfume reference sample); press "Ok". The instrument calculates and prints the DeltaE value between the selected sample and reference. Record this value.

7. Test Method for Determining the Logarithm of the Octanol/Water Partition Coefficient (Log P)

The value of the log of the Octanol/Water Partition Coefficient (log P) is computed for each PRM in the perfume mixture being tested. The log P of an individual PRM is calculated using the Consensus log P Computational Model, version 14.02 (Linux) available from Advanced Chemistry Development Inc. (ACD/Labs) (Toronto, Canada) to provide the unitless log P value. The ACD/Labs' Consensus log P Computational Model is part of the ACD/Labs model suite.

EXAMPLES

The examples provided below are intended to be illustrative in nature and are not intended to be limiting.

Example 1. Perfume Intensity Performance (Liquid Fabric Conditioner)

In the following example, a liquid consumer product composition (namely, a liquid fabric conditioning composition) is made; one sample includes only neat perfume (i.e., no particles—Sample 1), while the other includes particles according to the present disclosure, which include a graft copolymer and perfume raw materials (Sample 2). As shown by the data below, the composition that include the particles provide greater intensity of dry fabric odor compared to the composition having only neat perfume oil.

A. Preparation of a Polymer/Perfume Feedstock Composition

A polymer/perfume feedstock composition is prepared by adding perfume raw materials (Perfume Oil 2) to a graft copolymer in a 50:50 weight ratio. The graft copolymer is commercially available under the name SOLUPLUS™ (ex BASF), and is believed to comprise 13 wt % polyethylene glycol MW 6000, 57 wt % N-vinylcaprolactam, and 30 wt % vinyl acetate, and to be characterized by an average molecular weight of about 44,000 Daltons.

The mixture is homogenized with a stirring bar while heating at 60° C. (in a closed container). The obtained feedstock composition is cooled down by letting it rest in a room at 21° C.

When the feedstock composition is combined with the base fabric softener composition as described in the next section, particles according to the present disclosure are formed.

B. Preparation of a Liquid Consumer Product

Liquid fabric softener compositions are prepared in the following manner Water, chelant, HCl, formic acid, and preservative are mixed together in a glass beaker with a magnetic stirrer. This aqueous solution is heated up in an oven at 85° C. The fabric softener active (a diester quaternary ammonium compound—REWOQUAT™ CI-DEEDMAC, ex Evonik) is heated up in an oven at 85° C. The aqueous solution directly coming from oven is mixed with an overhead mixer. The fabric softener active directly coming from the oven is added into the hot water. The obtained dispersion is cooled down by letting it rest in a room at 21° C. The copolymer from vinylamine, vinylformamid, and the glycerol are added during overhead stirring. Perfume Oil 1 is added.

For Sample 1, Perfume Oil 2 (neat) is next added. For Sample 2, the polymer/perfume feedstock composition (described above; 50% Perfume Oil 2) is heated up to 60° C. in a closed container, is added to the base composition during overhead stirring, and is further dispersed using an ultraturax mixer 8,500 RPM for 60 seconds.

Next, for both Samples 1 and 2, the structurant is added during overhead stirring, and it is further dispersed with the overhead stirrer for 10 minutes.

The formulations of Samples 1 and 2 are provided below in Table 1.

TABLE 1

| Ingredient (wt %) | Sample 1 (comp.) | Sample 2 (inv.) |
|---|---|---|
| Softening active[1] | 9.50% | 9.50% |
| Formic acid | 0.045% | 0.045% |
| Hydrochloric acid | 0.010% | 0.010% |
| 1,2-benzisothiazolin-3-one | 0.0045% | 0.0045% |
| Sodium Hydroxyethane diphosphonic acid | 0.0071% | 0.0071% |
| Copolymer from Vinylamin, Vinylformamid | 0.0050% | 0.0050% |
| Glycerol | 3.0% | 3.0% |
| Perfume oil 1 | 0.50% | 0.50% |
| Perfume oil 2 (neat) | 0.15% | — |
| Polymer/perfume (50:50) feedstock composition | — | 0.300% |
| Structurant | 0.20% | 0.20% |
| Water - balance to 100% | balance | balance |

[1] Diester quaternary ammonium compound (Ci-DEEDMAC = Ditallowoyl Ethoxy Ester Dimethyl Ammonium Chloride [MDEA based, Methyl Di-Ethanol amine based quat, available from Evonik])

B. Fabric Treatment Method

To treat the fabrics of with Samples 1 and 2, the following method is followed. For each treatment, a washing machine (ex Miele) is loaded with about 3 kg of a fabric load. The fabric load comprises about 1065 g knitted cotton fabric and about 1065 g polyester-cotton fabrics (50/50). Additionally, the fabric load comprises twenty terry towel tracers, which weigh together about 870 g.

Before the wash, the machine is cleaned out. In total 4 ethanol wipes are used: one for the first half of the inox drum; another one for the second half of the inox drum; the third wipe for the rubber of the washing machine; the fourth for the washing machine drawer. The washing machine is left open for minimum one minute. Then one washing cycle is run at 95° C.

Prior to the test treatment, the load is preconditioned twice, each time using the 95° C. short cotton cycle with 79 g of unperfumed IEC A Base detergent (ex WFK Testgewebe GmbH), followed by two additional 95° C. washes without detergent.

For the test treatment, the load is washed using a 40° C. short cotton cycle, 1200 rpm spin speed with 79 g IEC A Base detergent, which is added at the start of the wash cycle in the appropriate dispenser. A dosage of 40 ml of test fabric treatment composition (e.g., according to Samples 1 and 2) is added in the appropriate dispenser.

C. Perfume Intensity Evaluation

For each test composition, the fabric treatment method is performed twice, once for the "wet" touchpoint evaluation, and once for the "dry" touchpoints. For the wet touchpoint, the terry towel tracers are evaluated while wet for perfume intensity. For the dry touchpoint, the terry towels are line dried after the fabric treatment and evaluated the next day for perfume intensity.

Perfume intensity evaluation is conducted by a trained panel. The panel grades on a perfume odor intensity scale from 0 to 100, where 0=no perfume odor, 25=slight perfume odor, 50=moderate perfume odor, 75=strong perfume odor, and 100=extremely strong perfume odor. Fabrics are evaluated for perfume intensity at the wet, dry, and/or rub touchpoints.

D. Test Results

Perfume odor intensity results at the wet and dry touchpoints are provided in Table 2. Additionally, the difference in intensity values is provided, showing the performance difference between the composition with perfume/polymer delivery particles (e.g., Sample 2) and the comparative sample with only neat perfume oil (Sample 1).

TABLE 2

| | Perfume odor intensity | | |
|---|---|---|---|
| | Sample 1 (neat/comp.) | Sample 2 (particles/inv.) | Delta (Sample 2 − Sample 1) |
| WET touchpoint | 59.1 | 60.6 | +1.5 |
| DRY touchpoint | 24.5 | 33.7 | +9.2* |

*Statistically significant at a 90% confidence interval

As shown by the results in Table 2, Sample 2, in which some of the perfume oil was added as a polymer/perfume feedstock composition thereby leading to particles in the fabric softener composition, provides improved perfume odor intensity compared to Sample 1, in which the perfume was added as neat perfume oil. The difference appears significant at the DRY touchpoint and directional at the WET touchpoint.

Example 2. Perfume Intensity Performance (Hard Surface Cleaner)

In the following example, a liquid consumer product composition (namely, an aqueous hard surface cleaner) is made. As shown by the data below, particles according to the present disclosure can be used to effectively incorporate a benefit agent (namely, perfume raw materials) into such compositions.

A. Preparation of a Polymer/Perfume Feedstock Composition

A polymer/perfume feedstock composition is made by adding perfume oil to a graft copolymer in a 50:50 weight ratio. The graft copolymer is Soluplus™, ex BASF, as described in Example 1. The perfume oil comprises a majority, by weight, of perfume raw materials that are characterized as a mixture of Quadrant III PRMs and Quadrant IV PRMs. The mixture is homogenized by mixing with a stirring bar while heating at 60° C. in a closed container. The resulting feedstock composition is cooled by letting the mixture rest at ambient temperature (about 21° C.).

B. Hard Surface Cleaner ("HSC") Compositions

A hard surface cleaner base composition according to Table 3, below, is provided.

TABLE 3

| Ingredient | Wt % |
|---|---|
| Water (deionized) | 93.835% |
| C12/14 amine oxide | 0.375% |
| Anionic surfactant (dodecyl benzene sulphonic acid) | 0.375% |
| Nonionic surfactant (ethoxylated alcohol) | 2.4% |
| Dyes | 0.01% |
| Anti-foam | 0.15% |
| Citric acid | 0.6% |
| NaOH | 0.52% |
| Carbonate | 0.9% |
| Diethylenetriamine penta(methylene phosphonic acid) | 0.4% |

TABLE 3-continued

| Ingredient | Wt % |
|---|---|
| Preservative | 0.015% |
| Perfume oil | 0.42% |

To several samples of the HSC base composition, a portion of the perfume/polymer feedstock composition of part A is added, so that the feedstock is present at 1% and 2%, respectively, in the resulting HSC composition, resulting in approximately 0.5% and 1% of perfume added via the feedstock composition. A portion of the HSC base composition is provided as-is, where no feedstock composition is added.

Additionally, a commercially available HSC composition is provided: AJAX "Tornade de Proprete" Lemon, as sold in Belgium.

C. Test Results

The compositions are diluted (30 mL in 2.5 L cold tap water) in a bucket, and each resulting mixture is used to treat a hard surface floor via mopping with a microfiber-strip implement. After treatment, each room is evaluated for perfume odor intensity at different time intervals (0 hours; 1.5 hours; 2.5 hours). Perfume odor intensity is assessed according to same scale as provided in Example 1.

Additionally, the compositions placed in glass containers and are visually assessed for transparency.

The results are provided below in Table 4. For odor intensity, cells in a row that are not connected by the same letter are deemed to be significantly different at a 90% degree of confidence.

TABLE 4

| | Sample 3 (comp.) | Sample 4 | Sample 5 | Sample 6 (comp.) (comp. = AJAX product) |
|---|---|---|---|---|
| HSC base composition | 100% | 99% | 98% | N/A |
| Feedstock composition | — | 1% | 2% | N/A |
| Odor intensity (0 h) | 50.7 B | 62.2 A | 61.1 A | 53.9 B |
| Odor intensity (1.5 h) | 22.7 C | 29.4 B | 37.9 A | 23.0 C |
| Odor intensity (2.5 h) | 12.6 B | 12.5 B | 23.0 A | 13.4 B |
| Visual appearance | Yellow/clear | Yellow/clear | Yellow/hazy | Yellow/opaque |

As shown in Table 4, Sample 5 provides significantly more perfume odor intensity at each of the tested time intervals compared to Samples 3 and 6; Sample 4 provides significantly more odor intensity at time 0 h and 1.5 h.

Furthermore, the data in Table 4 indicates that when the feedstock is added at certain levels, the visual appearance of the HSC composition can be maintained (e.g., remain substantially transparent).

Additionally (and not shown in Table 4), a composition comparable to Sample 4 is created ("4B"), in which the same amount and type of the feedstock's perfume (0.5% of final composition) is added neat (e.g., no polymer) to the HSC base composition. The resulting "4B" HSC composition is hazy, apparently as a result of the hydrophobic perfume raw materials, whereas Sample 4 is substantially clear. This indicates that adding perfume as part of the polymer/perfume feedstock composition aids the perfume's solubility/dispersibility in the aqueous HSC composition. The 4B composition is not tested for odor intensity.

Example 3. Particles Containing Lipase

A feedstock composition is made by mixing Soluplus™ polymer (as described above) with fluorescently-labeled lipase enzyme (Lipex™, ex Novozymes). The feedstock composition is added to a liquid base composition, where the base composition is suitable for making a compact/soluble unit dose detergent product (35-45% surfactant; 5-15% water).

Under the fluorescent light of a confocal microscope, the lipase enzyme appears as colloidal aggregates. It is believed that the colloidal aggregates correlate with solid matter such as particles according to the present disclosure, where the lipase enzyme is coupled with the Soluplus™ polymer.

Example 4. Particles Containing an Antimicrobial Agent

A feedstock composition is made by mixing Soluplus™ polymer with an antimicrobial agent, methylglyoxal (ex Sigma Aldrich). The feedstock composition is added to a liquid base composition, where the base composition is suitable for making a liquid hand-dishwashing composition (20-25% surfactant).

As such compositions containing methylglyoxal are typically known to discolor over time, the composition is observed for discoloration upon ageing. The tested composition appears to discolor less than expected.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making a liquid consumer product composition, the method comprising the steps of:
   providing a liquid feedstock composition comprising a benefit agent and a graft copolymer, the graft copolymer comprising a polyalkylene glycol as a graft base and one or more side chains that comprise vinyl acetate moieties and N-vinylcaprolactam moieties;

combining the feedstock composition with a base composition, the base composition comprising a consumer product adjunct, wherein the resulting liquid consumer product composition comprises delivery particles that comprise the benefit agent and the graft copolymer, wherein the delivery particles are characterized by a number-average diameter of from about 0.5 microns to about 5000 microns;

wherein the liquid consumer product composition is a fabric care composition, a hard surface cleaner composition, a dish care composition, a hair care composition, a body cleansing composition, or a mixture thereof.

2. The method according to claim 1, wherein the liquid consumer product composition comprises from about 1% to about 99%, by weight of the composition, of water.

3. The method according to claim 1, wherein the graft copolymer is characterized by a weight average molecular weight from about 2000 Daltons to about 500,000 Daltons.

4. The method according to claim 1, wherein the graft base is characterized by a weight average molecular weight of from about 2000 to about 15,000 Daltons.

5. The method according to claim 1, wherein the polyalkylene glycol of the graft copolymer comprises polyethylene glycol ("PEG").

6. The method according to claim 1, wherein the weight ratio of vinyl acetate moieties to vinylcaprolactam moieties is from about 1:10 to about 10:1.

7. The method according to claim 1, wherein the weight ratio of the sum of the vinyl acetate moieties and vinylcaprolactam moieties to the polyalkylene glycol (e.g., side chains:graft base) is from about 1:2 to about 10:1.

8. The method according to claim 1, wherein the graft copolymer is obtainable from:
i) 50 to 60 wt % N-vinylcaprolactam,
ii) 25 to 35 wt % vinyl acetate, and
iii) 10 to 20 wt % of the polyalkylene glycol,
with the proviso that the sum of components i), ii), and iii) is equal to about 100 wt %.

9. The method according to claim 1, wherein the graft copolymer comprises about 13 wt % polyethylene glycol having MW 6000, about 57 wt % N-vinylcaprolactam, and about 30 wt % vinyl acetate.

10. The method according to claim 1, wherein the benefit agent is present in an amount of from about 0.01% to about 5%, by weight of the composition.

11. The method according to claim 1, wherein the benefit agent is selected from the group consisting of perfume raw materials, silicone oils, waxes, hydrocarbons, higher fatty acids, essential oils, lipids, skin coolants, vitamins, sunscreens, antioxidants, glycerine, catalysts, bleach particles, silicon dioxide particles, malodor reducing agents, odor-controlling materials, chelating agents, antistatic agents, softening agents, insect and moth repelling agents, colorants, antioxidants, chelants, bodying agents, drape and form control agents, smoothness agents, wrinkle control agents, sanitization agents, disinfecting agents, germ control agents, mold control agents, mildew control agents, antiviral agents, drying agents, stain resistance agents, soil release agents, fabric refreshing agents and freshness extending agents, chlorine bleach odor control agents, dye fixatives, dye transfer inhibitors, color maintenance agents, optical brighteners, color restoration/rejuvenation agents, anti-fading agents, whiteness enhancers, anti-abrasion agents, wear resistance agents, fabric integrity agents, anti-wear agents, anti-pilling agents, defoamers, anti-foaming agents, UV protection agents for fabrics and skin, sun fade inhibitors, anti-allergenic agents, enzymes, water proofing agents, fabric comfort agents, shrinkage resistance agents, stretch resistance agents, stretch recovery agents, skin care agents, glycerin, natural actives, aloe vera, vitamin E, shea butter, cocoa butter, brighteners, antibacterial actives, antiperspirant actives, cationic polymers, dyes, hueing dyes, skin heath agents, skin restoration agents, anti-skin-aging agents, facial contrast agents, anti-dandruff agents, skin lightening agents, anti-acne agents, emollients, non-steroidal anti-inflammatory agents, topical anaesthetics, artificial tanning agents, anti-microbial and anti-fungal actives, skin soothing agents, skin barrier repair agents, anti-skin atrophy actives, lipids, sebum inhibitors, sebum inhibitors, skin sensates, protease inhibitors, anti-itch agents, desquamation enzyme enhancers, anti-glycation agents, and mixtures thereof.

12. The method according to claim 1, wherein the benefit agent is selected from the group comprises perfume raw materials.

13. The method according to claim 12, wherein the perfume raw materials comprise materials selected from Quadrant III perfume raw materials, Quadrant IV perfume raw materials, or mixtures thereof,
and optionally:
wherein the liquid consumer product composition comprises at least 60%, by weight of the composition, of water, and/or less than 10%, by weight of the composition, of surfactant.

14. The method according to claim 1, wherein the benefit agent comprises enzymes.

15. The method according to claim 1, wherein the composition is encapsulated in a water-soluble film.

16. The method according to claim 1, wherein the consumer product adjunct is selected from an amine, a surfactant system, a water-binding agent, a sulfite, fatty acids and/or salts thereof, enzymes, encapsulated benefit agents, soil release polymers, hueing agents, builders, chelating agents, dye transfer inhibiting agents, dispersants, enzyme stabilizers, catalytic materials, bleaching agents, bleach catalysts, bleach activators, polymeric dispersing agents, soil removal/anti-redeposition agents, polymeric dispersing agents, polymeric grease cleaning agents, brighteners, suds suppressors, dyes, hueing agents, free perfume, structure elasticizing agents, fabric softening agents, carriers, fillers, hydrotropes, organic solvents, anti-microbial agents and/or preservatives, neutralizers and/or pH adjusting agents, processing aids, fillers, rheology modifiers or structurants, opacifiers, pearlescent agents, pigments, anti-corrosion and/or anti-tarnishing agents, and mixtures thereof.

17. The method according to claim 1, wherein consumer product adjunct comprises a surfactant system, fabric softeners, or combinations thereof.

* * * * *